United States Patent
Kondo et al.

(10) Patent No.: US 8,520,017 B2
(45) Date of Patent: Aug. 27, 2013

(54) SYSTEM AND METHOD FOR MANAGING AND DISPLAYING MEDICAL IMAGES

(75) Inventors: Takashi Kondo, Otawara (JP); Kenichi Niwa, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 773 days.

(21) Appl. No.: 11/118,350

(22) Filed: May 2, 2005

(65) Prior Publication Data

US 2005/0251020 A1 Nov. 10, 2005

(30) Foreign Application Priority Data

Apr. 30, 2004 (JP) ................................. 2004-135921

(51) Int. Cl.
*G06T 1/60* (2006.01)
*G09G 5/00* (2006.01)
*G06K 9/00* (2006.01)

(52) U.S. Cl.
USPC ........... 345/530; 345/619; 345/629; 382/128; 382/131; 382/132; 705/2; 705/3

(58) Field of Classification Search
USPC ................. 345/530, 619, 629; 382/128–133; 704/2–3; 707/1
See application file for complete search history.

(56) References Cited

U.S. PATENT DOCUMENTS

| | | | | |
|---|---|---|---|---|
| 5,172,103 | A * | 12/1992 | Kita | 345/667 |
| 7,058,901 | B1 * | 6/2006 | Hafey et al. | 715/792 |
| 7,170,532 | B2 * | 1/2007 | Sako | 345/637 |
| 2002/0101436 | A1 | 8/2002 | Shastri et al. | |
| 2005/0110788 | A1 * | 5/2005 | Turner et al. | 345/419 |

FOREIGN PATENT DOCUMENTS

JP 4-49946 2/1992

* cited by examiner

*Primary Examiner* — Tize Ma
(74) *Attorney, Agent, or Firm* — Oblon, Spivak, McClelland, Maier & Neustadt, L.L.P.

(57) ABSTRACT

A system for managing and displaying medical images, comprising an associating unit for associating image file, including a medical image data, with a display mode data held at least a screen division and a image segment including a medical image, and an image display unit for displaying the medical image data included the image file as a medical image on the screen in accordance with the display mode data associating with the image file.

19 Claims, 16 Drawing Sheets

BLANK AREA

PATIENT DEMOGRAPHIC AREA

| (0010, 0010) | TOKKYO TARO |
| (aaaa, 0001) | 123456789-0 |
| (bbbb, 0002) | 1942/12/25 |
| (cccc, 0003) | CT |
| (dddd, 0004) | 1111. 2222. 3333. 4444 |
| (eeee, 0005) | |

...

| (ffff, 0006) |

IMAGE DATA AREA

| DISPLAY MODE DATA $I_{CT-1}$ | 2×2, (1,1), S0 |
|---|---|
| DISPLAY MODE DATA $I_{CT-2}$ | 2×2, (1,2), S1 |
| DISPLAY MODE DATA $I_{CT-3}$ | 2×2, (1,2), S2 |
| DISPLAY MODE DATA $I_{CT-4}$ | 2×2, (2,2), S1 |
| DISPLAY MODE DATA $I_{CT-5}$ | 2×2, (2,1), S2 |
| DISPLAY MODE DATA $I_{CT-6}$ | 2×2, (2,1), S3 |
| ... | ... |

FIG. 6

BLANK AREA

PATIENT DEMOGRAPHIC AREA

| (0010, 0010) | TOKKYO TARO |
| (aaaa, 0001) | 123456789-0 |
| (bbbb, 0002) | 1942/12/25 |
| (cccc, 0003) | CT |
| (dddd, 0004) | 1111. 2222. 3333. 4444 |
| (ffff, 0005) | 2×2,(1,1),S0 |

⋮

| (ffff, 0006) |

IMAGE DATA AREA

| DISPLAY MODE DATA $I_{CT-1}$ | 2×2, (1, 2), S, 0.5 |
|---|---|
| DISPLAY MODE DATA $I_{CT-2}$ | 2×2, (1, 2), S, 0.5 |
| DISPLAY MODE DATA $I_{MR-1}$ | 2×2, (2, 2), S, 1 |
| DISPLAY MODE DATA $I_{MR-2}$ | 2×2, (2, 2), S, 1 |
| DISPLAY MODE DATA $I_{MR-3}$ | 2×2, (2, 2), S, 1 |
| DISPLAY MODE DATA $I_{CR}$ | 2×2, (1, 1)−(2, 1), 0, 1 |
| ... | |

FIG. 10A

| DISPLAY MODE DATA $I_{CT-1}$ | 2×2, CT−(1, 2), CT−S, CT−0. 5, MR−(2, 2), MR−S, MR−1, CR−(1, 1)−(2−1), CR−0, CR−1 |
|---|---|
| DISPLAY MODE DATA $I_{CT-2}$ | 2×2, CT−(1, 2), CT−S, CT−0. 5, MR−(2, 2), MR−S, MR−1, CR−(1, 1)−(2−1), CR−0, CR−1 |
| DISPLAY MODE DATA $I_{MR-1}$ | 2×2, CT−(1, 2), CT−S, CT−0. 5, MR−(2, 2), MR−S, MR−1, CR−(1, 1)−(2−1), CR−0, CR−1 |
| DISPLAY MODE DATA $I_{MR-2}$ | 2×2, CT−(1, 2), CT−S, CT−0. 5, MR−(2, 2), MR−S, MR−1, CR−(1, 1)−(2−1), CR−0, CR−1 |
| DISPLAY MODE DATA $I_{MR-3}$ | 2×2, CT−(1, 2), CT−S, CT−0. 5, MR−(2, 2), MR−S, MR−1, CR−(1, 1)−(2−1), CR−0, CR−1 |
| DISPLAY MODE DATA $I_{CR}$ | 2×2, CT−(1, 2), CT−S, CT−0. 5, MR−(2, 2), MR−S, MR−1, CR−(1, 1)−(2−1), CR−0, CR−1 |
| ... | |

FIG. 10B

| | |
|---|---|
| DISPLAY MODE DATA I<sub>CT-1</sub> | A12345, 2×2, (1, 1), S0 |
| DISPLAY MODE DATA I<sub>CT-2</sub> | A12345, 2×2, (1, 2), S1 |
| DISPLAY MODE DATA I<sub>CT-3</sub> | A12345, 2×2, (1, 2), S2 |
| DISPLAY MODE DATA I<sub>CT-4</sub> | A12345, 2×2, (2, 1), S1 |
| DISPLAY MODE DATA I<sub>CT-5</sub> | A12345, 2×2, (2, 1), S2 |
| DISPLAY MODE DATA I<sub>CT-6</sub> | A12345, 2×2, (2, 1), S3 |
| ... | ... |

FIG. 11

| CLASSIFICATION OF THE MEDICAL IMAGE DATA | DISPLAY MODE DATA I |
|---|---|
| CT IMAGE DATA | 2×2, CT-(1, 1)-(2, 2), CT-S, CT-0. 5 |
| MR IMAGE DATA | 2×2, MR-(1, 1)-(2, 2), MR-S, MR-1 |
| CR IMAGE DATA | 2×2, CR-(1, 1)-(2, 2), CR-0, CR-1 |
| CT IMAGE DATA + MR IMAGE DATA | 2×2, CT-(1, 1), CT-S, CT-0. 5, MR-(2, 2), MR-S, MR-1 |
| CT IMAGE DATA + MR IMAGE DATA + CR IMAGE DATA | 2×2, CT-(1, 2), CT-S, CT-0. 5, MR-(2, 2), MR-S, MR-1, CR-(1, 1)-(2-1), CR-0, CR-1 |
| ... | ... |

FIG. 14

SYSTEM AND METHOD FOR MANAGING AND DISPLAYING MEDICAL IMAGES

BACKGROUND OF THE INVENTION

1. Field of the Invention

The present invention relates to a system for storing and displaying images formed from an image storage server for storing image data and an image display unit connected to the image storage server via a network.

2. Description of the Related Art

Medical imaging diagnosis is the process in which a doctor makes a diagnosis based on medical images (i.e., the doctor interprets the medical images) developed on a film or output on an image display unit. The medical images to be interpreted are captured by various modalities (i.e., medical imaging devices), such as computed tomography (CT), computed radiography (CR), magnetic resonance (MR), and digital radiography (DR).

Recently, medical image data management systems, such as a picture archiving and communication system (PACS), have been widely used. By using PACS at a medical facility, such as a hospital, a system enabling transmission of medical image data between an image storage server and an image display unit, such as a workstation, can be established.

The image storage server stores, in advance, medical images from various modalities and relates the medical images from each modality with a predetermined display mode (layout) for a display screen that is most appropriate for interpreting the medical image obtained by the particular modality. When a modality is selected, the best display mode for the selected modality is also selected to display medial images on the PACS image display unit (for example, refer to Japanese-Unexamined Patent Application Publication No. 4-49945).

For example, if a plurality of CT images of a patient is displayed on the PACS image display unit, the user of the PACS can categorize the CT images according to the different regions of the body, such as the head, the chest region, and the abdominal region. Then the display mode for the CT images of each category may be changed on the image display unit.

However, when interpreting a plurality of medical images obtained from various modalities, the display mode of the medical images had to be changed at a client viewer by a user to the optimal display mode for interpreting the medical images. This operation places a great burden on the user. Furthermore, since devices that are capable of easily and quickly scanning the entire human body, such as a multi-slice CT device, have been introduced, it is difficult for the user to categorize the medical images obtained from the series of data. For this reason, the medical images obtained from a series of data were often not categorized appropriately. As a result, this inappropriate categorization led to a misinterpretation of the medical images by the user.

When the user categorizes the medical images, the identification numbers of the categorized medical images must be stored in a database of the image data server. Also, the identification numbers of the medical images must be displayed on the client viewer. The transmission of these identification numbers has been adding load to the network.

For a multiple modality viewer capable of displaying images from a plurality of modalities, a display capable of efficiently displaying the images of a patient captured by the plurality of modalities on the same screen is desired. However, according to known display modes, only the optimal display mode for a single modality could be selected. As a result, the medical images captured by the plurality of modalities overlapped each other on the screen in the initial display mode. Hence, the display mode had to be changed at the image display unit to a mode that facilitated the interpretation of the medical images. This operation causes the working efficiency for the user to be reduced.

Moreover, when changing the display mode to a mode that facilitates the interpretation of the medical images at the client viewer, an application for changing the mode has to be installed in the client viewer. Sometimes, a multiple modality viewer is required to use image data such as computer aided diagnosis or detection (CAD) data to display similar images on the screen of the client viewer or to box off a predetermined image and line up similar images next to the boxed off image. Furthermore, new types of images that require new display modes may be introduced in the future. For this reason, it is predictable that in the future a wide variety of applications will be installed in the client viewer.

SUMMARY OF THE INVENTION

The present invention has taken into consideration the above-described problems and provides a system and method for displaying and managing medical images such that the medical images are displayed in an appropriate display mode at the initial settings and the working efficiency for the user is improved.

The present invention provides a system and method for displaying and managing medical images that do not require medical images to be categorized and stored according to identification numbers and that is capable of reducing the load on the network.

To solve the above-described problems, a system for managing and displaying medical images according to an aspect of the present invention comprises an associating unit for associating image file, including a medical image data, with a display mode data held at least a screen division and a image segment including a medical image, and an image display unit for displaying the medical image data included the image file as the medical image on the screen in accordance with the display mode data associating with the image file.

To solve the above-described problems, a method for managing and displaying medical images according to an aspect of the present invention includes steps of (A) memorizing an image file including a medical image data, (B) associating the image file with a display mode data held at least a screen division and an image segment including the medical image, and (C) displaying the medical image data included the image file as a medical image on a screen in accordance with the display mode data associating with the image file.

BRIEF DESCRIPTION OF THE DRAWINGS

FIG. 2 illustrates a sample of a structure of a DICOM file;

FIG. 6 illustrates a sample of a display mode data as a table;

FIG. 7 is a flow chart of a method for managing and displaying medical images according to another embodiment of the present invention;

FIG. 10A and FIG. 10B illustrate a sample of the display mode data as a table;

FIG. 11 illustrates a sample of the display mode data I as a table;

FIG. 14 illustrated a sample of the display mode data I as a table;

DESCRIPTION OF THE PREFERRED EMBODIMENTS

A system and a method for managing and displaying medical images according to embodiments of the present invention will be described below with reference to the drawings.

Figure 1:
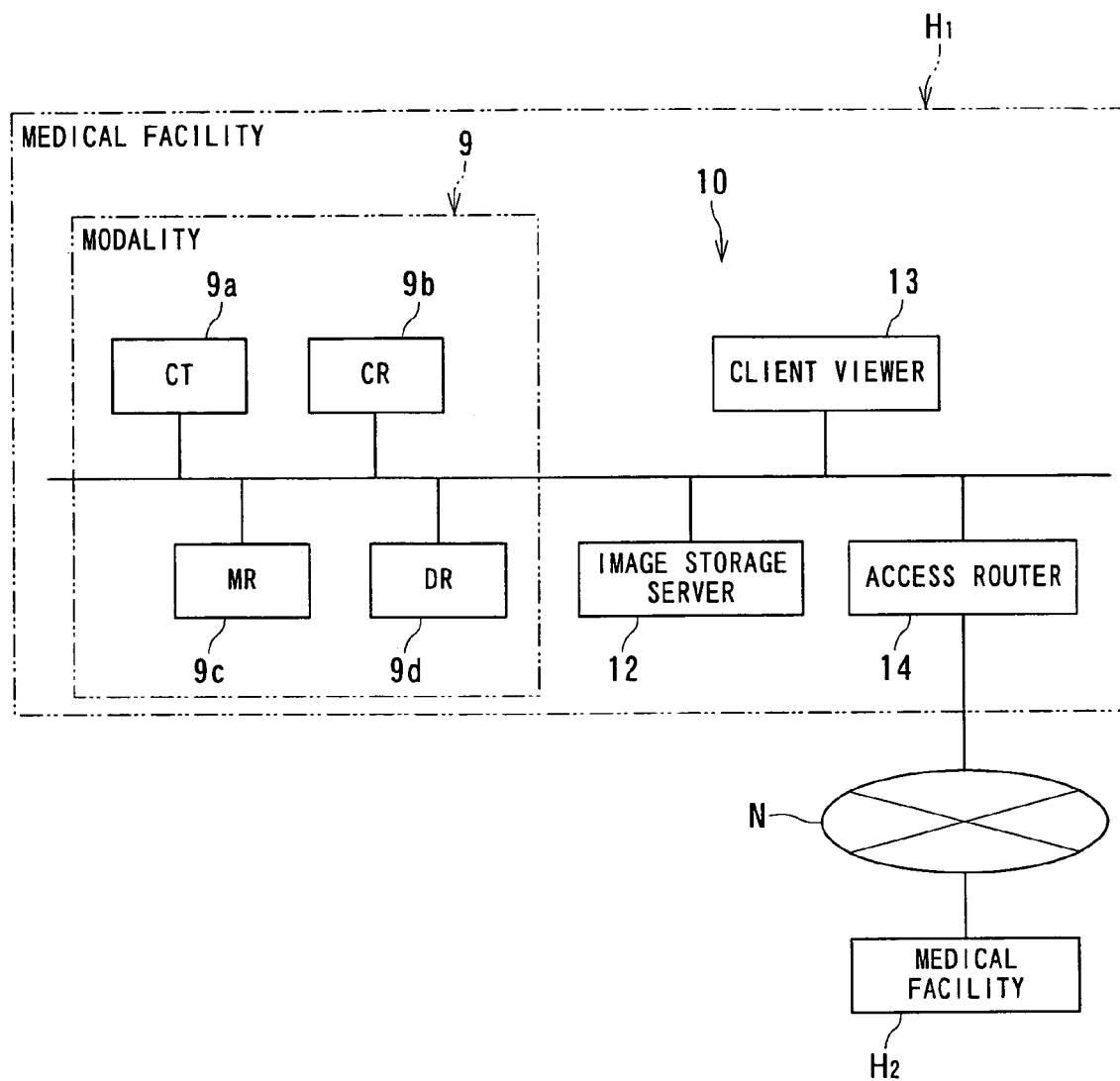
FIG. 1 is a schematic view of the entire system for managing and displaying medical images.
Figure 3:
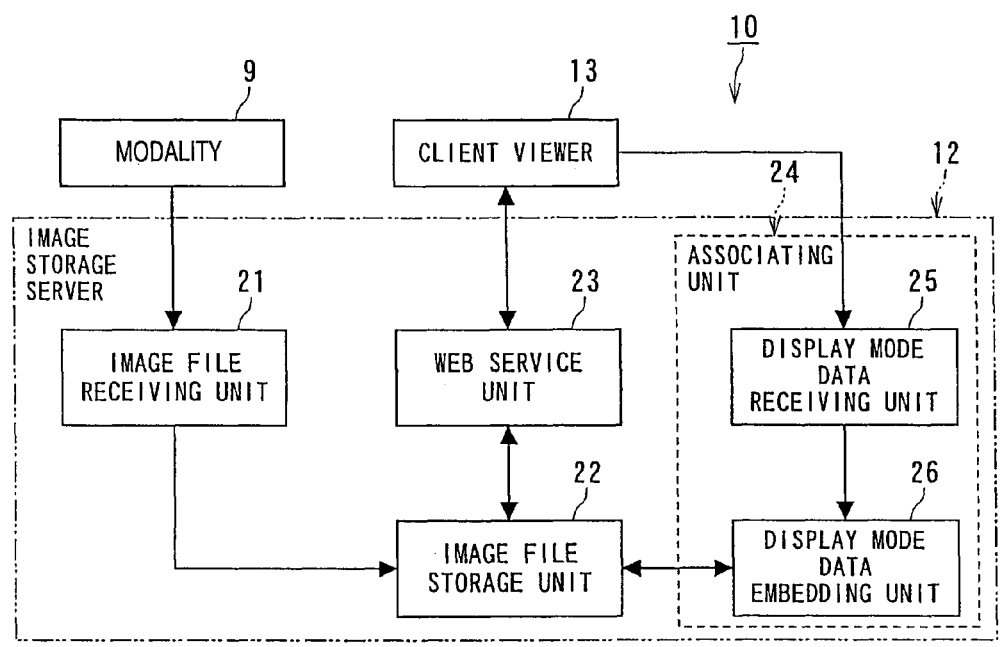
FIG. 3 is a block diagram illustrating an image storage server according to a first embodiment of the present invention.

FIGS. 1 and 3 illustrate a system for managing and displaying medical images according to a first embodiment of the present invention. FIG. 1 illustrates the entire system for managing and displaying the medical images.

As illustrated in FIG. 1, medical facilities $H_1$, $H_2$, ..., $H_n$ (only medical facilities $H_1$ and $H_2$ are shown in the drawing) are connected via a network N so that they are capable of transmitting data with each other. The network N may be established by a wire connection, such as a public line including an integrated services digital network (ISDN) or a dedicated line, or an open network, such as the Internet.

The medical facility $H_1$ includes the modality (medical imaging devices) 9 of the singular or the plural and a system 10 for managing and displaying medical images according to the present invention. The modality 9 is for generating Digital Imaging and Communication in Medicine (DICOM) files, which are a type of image files, from medical images, such as bitmap files, made by imaging.

The modality 9 is, for example, a computed tomography (CT) device 9a, a magnetic resonance (MR) device 9b, a computed radiography (CR) device 9c, or a digital radiography (DR) device 9d.

The system 10 for managing and displaying medical images includes an image storage server 12 for obtaining the DICOM files, generated at the modality 9, and for storing and managing these DICOM files, a client viewer 13 that is an image display unit for displaying the medical images by loading the DICOM files from the image storage server 12, and an access router 14 that is a communication unit for transmitting data between the medical facilities $H_1$ and $H_2$ via the network N.

A medical image data management system, such as a picture archiving and communication system (PACS) is established by connecting the image storage server 12 of a medical facility, such as a hospital, and the client viewer 13 capable of displaying the images, such as a workstation, via a network.

The DICOM files do not necessarily have to be generated at the modality 9 and, instead, may be generated at, for example, the image storage server 12.

As illustrated in FIG. 1, one client viewer 13 may be provided for the medical facility $H_1$ or a plurality of client viewers may be provided. The client viewer 13 includes a Web browser (not shown in the drawing) and a graphical user interface (GUI) (also not shown in the drawing). The Web browser is an application software program for loading the DICOM files and for analyzing the display mode of the medical images and displaying the medical images in accordance with the display mode. The GUI is for displaying graphical elements, such as icons and buttons, corresponding to commands related to image display and processing, such as the number of image segments and a type of image processing, and for operating these graphical elements with a pointing device, such as a mouse.

The DICOM files are generated at the modality 9 in accordance with the DICOM standard. The DICOM standard is a standard established in the United States for sharing medical data.

FIG. 2 illustrates a sample of a structure of a DICOM file.

As illustrated in FIG. 2, a DICOM file is a collection of data elements (1), (2), . . . , (n). Each data element includes a standard tag (group number and element number) and that tag data (data length and tag data). The tag data is attribute data related to the medical images, such as data about a patient, an imaging condition, an image, an display, and so on.

The patient data includes data that identifies the patient, such as a patient's name ID (IDentification) and a birth date; the imaging condition data includes data on the type of the medical image, such as a primary or a secondary image, an imaged region of the body, and an imaging condition, such as a X-ray tube current value and voltage value, of when imaging was carried out by the modality 9; the image data includes data on the examination ID and the type of modality 9; the display information includes information on the contrast of the image, the serial order and arrangement of the image, and the category number (the group ID for the group the medical image belongs to); and other data includes the file code of the DICOM file.

A tag and that tag data are embedded at the data patient demographic data area which a DICOM file, generated at the modality 9, composed of. For example, a tag which expresses the patient's name is "(0010,0010)" and that tag data is "TOKKYO TARO", a tag which expresses the patient's ID is "(aaaa,0001)" and that tag data "123456789-0", a tag which expresses the patient's birth date is "(bbbb,0002)" and that tag data is "1942/12/25", a tag which expresses the kind of the modality 9 is "(cccc,0003)" and that tag data is "CT", a tag which expresses the kind of a image ID is "(dddd,0004)" and that tag data is "1111.2222.3333.4444", and a tag which expresses the comment of examination is "(eeee,0005)", and a tag which expresses whether data following the rest is image data is "(ffff,0006)". Furthermore, tag and data length are embedded into the DICOM file as binary data. Tag data is embedded into the DICOM file as text data (character string) or binary data.

The modality 9, the image storage server 12, the client viewer 13, and the access router 14, illustrated in FIG. 1, are capable of transmitting data between each other via a local area network (LAN) 15, which is a network used inside the medical facility $H_1$.

Instead, the DICOM files, generated at the modality 9, may be recorded on a recording medium, such as a flexible disk (FD), a compact disk read only memory (CD-ROM), or a flash memory. In this way, the image storage server 12 can read out the DICOM files from these recording media.

FIG. 3 is a block diagram illustrating the image storage server 12.

The image storage server 12, illustrated in FIG. 3, includes an image file receiving unit 21 for receiving the DICOM files, generated at the modality 9 via the LAN 15, an image file storage unit 22 for storing therein the DICOM files received by the image file receiving unit 21, a Web service unit 23 for sending DICOM files, stored in the image file storage unit 22, in accordance with a request from a Web browser (not shown in the drawing) of the client viewer 13, and an associating unit 24 for associating the image files, including the medical image data, with the display mode data including at least a screen division and an image segment including the medical images. The associating unit 24 includes, for example a display mode data receiving unit 25 for receiving display mode data (data on the display mode of the medical images) from the client viewer 13 or viewer (not shown in the drawing) in medical facilities $H_2$, and a display mode data embedding unit 26 for embedding the display mode data, received from the display mode data receiving unit 25. In this case, at the associating unit 24, the display mode data is embedded into the DICOM files. However, associating is not limited to embed the display mode data into the DICOM files.

The image file storage unit 22 stores DICOM files F with embedded display mode data, generated at the display mode data embedding unit 26.

The file storage unit 22 also stores DICOM files F with embedded display mode data. The image storage server 12 retrieves these DICOM files F from the file storage unit 22, in accordance with a request from the client viewer 13. The Web service unit 23 sends these DICOM files F to the client viewer 13 via the LAN 15 and to other medical facilities $H_2$ via the network N.

When the images, acquired at one modality 9, are displayed on the client viewer 13 screen, The display mode data of these images may be embedded into the DICOM files at the modality 9.

Figure 4:
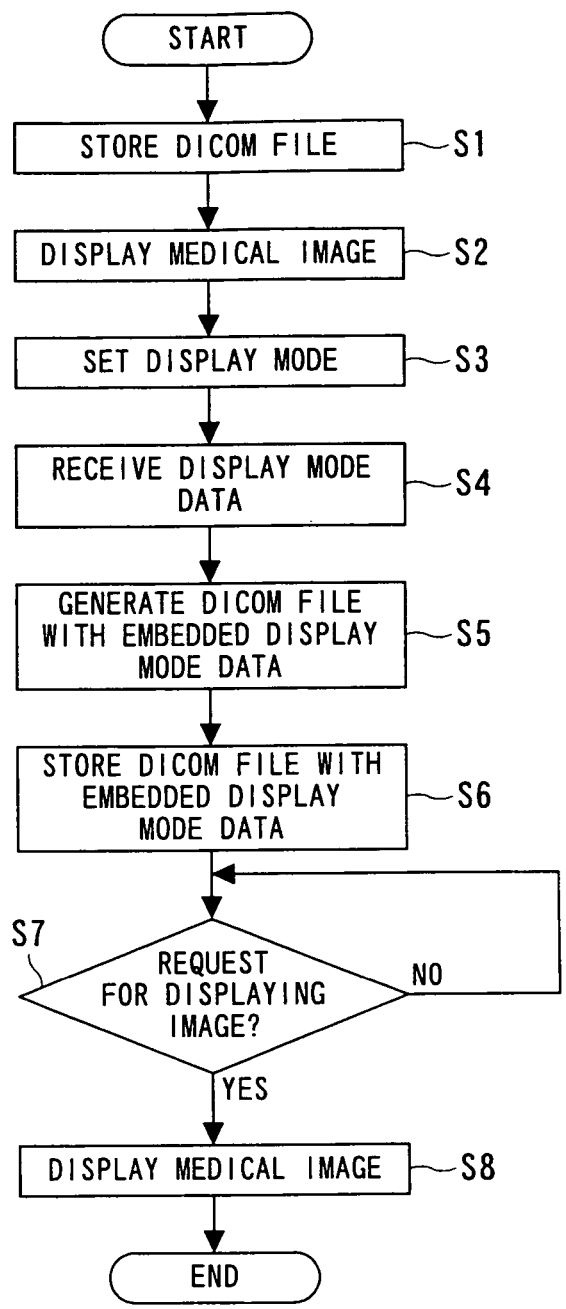
FIG. 4 is a flow chart illustrating a method for managing and displaying medical images according to an embodiment of the present invention.

Next, the method for managing and displaying medical images using the system 10 for managing and displaying medical images will be described with reference to the flow chart in FIG. 4. In this case, the modality used in the method is the CT device 9a. However, the modality of the method is not limited to a CT device.

First, when imaging for each patient is carried out by the CT device 9a, a DICOM file is generated for each CT image data, illustrated in FIG. 1. These DICOM files are composed of a blank area, a patient demographic data area, and an image data area. The patient demographic data area is composed of a collection of data elements. Each data element includes tags and that tag data conforming to the DICOM standard. In the data element included each DICOM file, tag and data length are embedded as binary data and tag data is embedded as text data (character string) or binary data.

A controlling unit (not shown in the drawing) controls the system to send the DICOM files to the image file receiving unit 21 of the image storage server 12, illustrated in FIG. 3, via the LAN 15 and to store the DICOM files in the image file storage unit 22 (Step S1). The DICOM files generated by the CT device 9a may be recorded on a recording medium, such as a FD, a CD-ROM, or a flash memory and the image storage server 12 may read out the DICOM files from the recording medium.

A user, such as a doctor or a nurse, turns on the power to start up the client viewer 13. The user operates a pointing device (not shown in the drawing), such as a mouse, to request for displaying the medical images about the patient M that is a certain patient.

DICOM files, including the medical image data, about the patient M is retrieved from the image file storage unit 22, stored in Step S1. These DICOM files are sent from the Web service unit 23 to the Web browser of the client viewer 13 via the LAN 15. If DICOM files, including the CT image data, about the patient M are stored at the image file storage unit 22, these DICOM files are sent to the Web browser of the client viewer 13. Using the DICOM files sent from the image storage server 12, the CT images of the patient M are displayed on the client viewer 13 screen (Step S2).

The user operates the pointing device, i.e., mouse, to organize the CT images through the GUI in an easily viewable arrangement. By dragging and dropping the CT images, the user changes at least one of the display modes, i.e., the screen division, the image segment including the image, whether or not the image is included in a stack, or the order of the image in the stack. Often in CT imaging, a plurality of body regions is captured in one imaging session. In such a case, the user may change the display mode to categorize the captured CT images according to the body regions.

Figure 5:
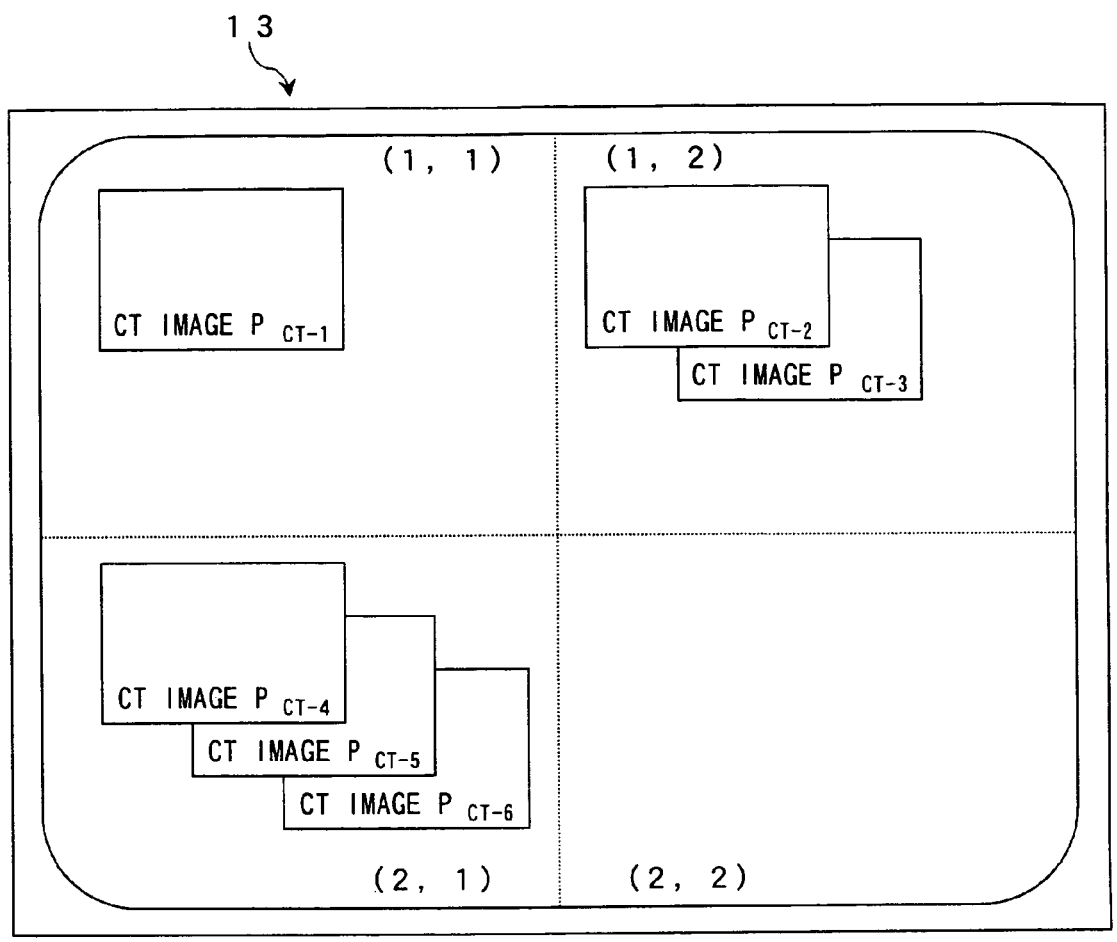
FIG. 5 illustrates a sample of a display mode of the CT images after the display mode has been changed on the client viewer screen.

FIG. 5 illustrates a sample of a display mode of the CT images after the display mode has been changed on the client viewer 13 screen.

FIG. 5 illustrates the client viewer 13 screen after the display mode of CT images $P_{CT}$ of the patient M has been changed in Step S2 such that the user can easily view the CT images. For example, there are six CT images as the CT images of the patient M, i.e., CT images $P_{CT-1}$, $P_{CT-2}$, $P_{CT-3}$, $P_{CT-4}$, $P_{CT-5}$, and $P_{CT-6}$.

The display screen, as illustrated in FIG. 5, is divided into "2×2" segments. The "(1,1)" segment displays the CT image $P_{CT-1}$ without stacking the image.

The "(1,2)" segment of the display screen divided into "2×2" segments displays the CT image $P_{CT-2}$ as the first image in a stack. The second image in the stack is the CT image $P_{CT-3}$.

The "(2,1)" segment of the display screen divided into "2×2" segments displays the CT image $P_{CT-4}$ as the first image in a stack. The second image in the stack is the CT image $P_{CT-5}$ and the third image in the stack is the CT image $P_{CT-6}$.

Next, the user carries out an operation to output the display mode data, such as clicking an output button on the client viewer 13 screen. Outputting the display mode data sets the display mode on the client viewer 13 screen (Step S3).

Once the display mode for the screen is set, the display mode data on every image is sent from the client viewer 13 to the display mode data I receiving unit 25 of the image storage server 12 via the LAN 15. For example, there are the display mode data $I_{CT-1}$, $I_{CT-2}$, $I_{CT-3}$, $I_{CT-4}$, $I_{CT-5}$, and $I_{CT-6}$ as the display mode data I.

FIG. 6 illustrates a sample of the display mode data I as a table.

FIG. 6 illustrates the display mode data $I_{CT-1}$, $I_{CT-2}$, $I_{CT-3}$, $I_{CT-4}$, $I_{CT-5}$ and $I_{CT-6}$, after the display mode for the screen of CT images $P_{CT-1}$, $P_{CT-2}$, $P_{CT-3}$, $P_{CT-4}$, $P_{CT-5}$, and $P_{CT-6}$ are set as illustrated in FIG. 5. The display mode data $I_{CT-1}$, $I_{CT-2}$, $I_{CT-3}$, $I_{CT-4}$, $I_{CT-5}$, and $I_{CT-6}$ include the screen division, the image segment including the image, whether or not the image is included in a stack, and the order of the image in the stack.

For example, the display mode data $I_{CT-1}$ to conform to CT image $P_{CT-1}$ is "2×2, (1,1), S0". That display mode data $I_{CT-1}$ represents that the screen division is "2×2", the image segment including the image $P_{CT-1}$ is "(1,1)", and the image $P_{CT-1}$ is not included in a stack, respectively. The display mode data $I_{CT-2}$ to conform to CT image $P_{CT-2}$ is "2×2, (1,2), S1". That display mode data $I_{CT-2}$ represents that the screen division is "2×2," the image segment including the image $P_{CT-2}$ is "(1,2)", and the image $P_{CT-2}$ is the first image in the stack, respectively. The display mode data $I_{CT-3}$ to conform to CT image $P_{CT-3}$ is "2×2, (1,2), S2". That display mode data $I_{CT-3}$ represents that the screen division is "2×2," the image segment including the image $P_{CT-3}$ is "(1,2)", and the image $P_{CT-3}$ is the second image in the stack, respectively. The display mode data $I_{CT-4}$ to conform to CT image $P_{CT-4}$ is "2×2, (2,1), S1". That display mode data $I_{CT-4}$ represents that the screen division is "2×2," the image segment including the image $P_{CT-4}$ is "(2,1)", and the image $P_{CT-4}$ is the first image in the stack, respectively. The display mode data $I_{CT-5}$ to conform to CT image $P_{CT-5}$ is "2×2, (2,1), S2". That display date $I_{CT-5}$ represents that the screen division is "2×2," the image segment including the image $P_{CT-5}$ is "(2,1)", and the image $P_{CT-5}$ is the second image in the stack, respectively. The display mode data $I_{CT-6}$ to conform to CT image $P_{CT-6}$ "2×2, (2,1), S3". That display mode data $I_{CT-6}$ represents that the screen division is "2×2," the image segment including the image $P_{CT-6}$ is "(2,1)", and the image $P_{CT-6}$ is the third image in the stack, respectively.

Next, the display mode data I sent from the client viewer 13, illustrated in FIG. 3, is received by the display mode data receiving unit 25 of the image storage server 12 (Step S4). Then this data is sent to the display mode data embedding unit 26. At the display mode data embedding unit 26, the display mode data I, received in Step S4, is embedded into each DICOM file to generate DICOM files F with embedded display mode data (Step S5). In the data element included each DICOM file, tag and data length are embedded as binary data and tag data is embedded as text data (character string) or binary data.

FIG. 7 illustrates a sample of the structure of a DICOM file F with embedded display mode data.

FIG. 7 illustrates DICOM files F with embedded display mode embedded into the patient demographic data area included each DICOM file. When the display mode is set on the client viewer 13 screen in Step S3, the display mode data I is embedded into the patient demographic data area included each DICOM File as tag data to conform to the standard tag. Furthermore, a tag data to conform to the standard tag, generated at the modality 9, is a blank, because use frequency isn't so large in that that tag data in management.

In this case, the display mode data I is embedded into the patient demographic data area as tag data to conform to the standard tag. However, an area to be embedded is not limited to the patient demographic data area. The display mode data I can be embedded into, for example, the patient demographic data area as a private tag which can be set up freely. The display mode data I is embedded into, for example, a blank area included in each DICOM File.

The DICOM files F with embedded display mode data, generated at the display mode data embedding unit 26, are stored in the image file storage unit 22 of the image storage server 12, illustrated in FIG. 3 (Step S6). The image storage server 12 enters a stand-by mode and waits for a request for displaying the medical images. At the same time, the image storage server 12 determines whether or not a request for displaying the medical images is made from the client viewer 13 (Step S7).

The request for displaying the medical images may be made from the client viewer 13 in the medical facility $H_1$, from other client viewers in the medical facility $H_1$, or from other medical facilities $H_2$ connected by the network N.

If an answer in Step S7 is determined to be "YES," i.e., a request is made from the client viewer 13 to display the medical images about the patient M, the DICOM files F for the patient M with embedded display mode about the patient M is retrieved from the image file storage unit 22, stored in Step S6. These DICOM files F are sent from the Web service unit 23 to the Web browser of the client viewer 13 via the LAN 15. For example, if the DICOM files $F_{CT-1}$, $F_{CT-2}$, $F_{CT-3}$, $F_{CT-4}$, $F_{CT-5}$, and $F_{CT-6}$ with embedded display mode data $I_{CT-1}$, $I_{CT-2}$, $I_{CT-3}$, $I_{CT-4}$, $I_{CT-5}$, and $I_{CT-6}$ stored in the image file storage unit 22 respectively, the DICOM files $F_{CT-1}$, $F_{CT-2}$, $F_{CT-3}$, $F_{CT-4}$, $F_{CT-5}$, and $F_{CT-6}$ are sent from the Web service unit 23 to the Web browser of the client viewer 13 via the LAN 15.

On the client viewer 13 screen, the CT images $P_{CT-1}$, $P_{CT-2}$, $P_{CT-3}$, $P_{CT-4}$, $P_{CT-5}$, and $P_{CT-6}$ of the patient M are displayed in accordance with the display mode data $I_{CT-1}$, $I_{CT-2}$, $I_{CT-3}$, $I_{CT-4}$, $I_{CT-5}$, and $I_{CT-6}$, respectively. In other words, the CT images $P_{CT-1}$, $P_{CT-2}$, $P_{CT-3}$, $P_{CT-4}$, $P_{CT-5}$, and $P_{CT-6}$ of the patient M are initially displayed on the client viewer 13 screen in a display mode illustrated in FIG. 5 (Step S8).

The user may operate the CT images $P_{CT-1}$, $P_{CT-2}$, $P_{CT-3}$, $P_{CT-4}$, $P_{CT-5}$, and $P_{CT-6}$ of the patient M, displayed in Step S8, through the GUI by dragging and dropping the CT images using a pointing device, such as a mouse, to arrange the CT images in an arrangement that is easily viewable for the user. Subsequently, the new display mode is output, and the newly set display mode data is written over the tag data of the DICOM files $F_{CT}$ for the patient M with embedded display mode data and the CT images $P_{CT}$. Then, the process is returned to Step S6.

If an answer in Step S7 is determined to be "NO," i.e., a request is not made from the client viewer 13 to display the medical images about the patient M, the display mode data is updated, and the process is returned to Step S7. Then, the image storage server 12 enters a stand-by mode and waits for a request for displaying the medical images.

Medical images captured by modality 9 other than the CT device 9a are also displayed in accordance with the tag data in the same manner as the image captured by the CT device 9a, as described above.

Figure 8:
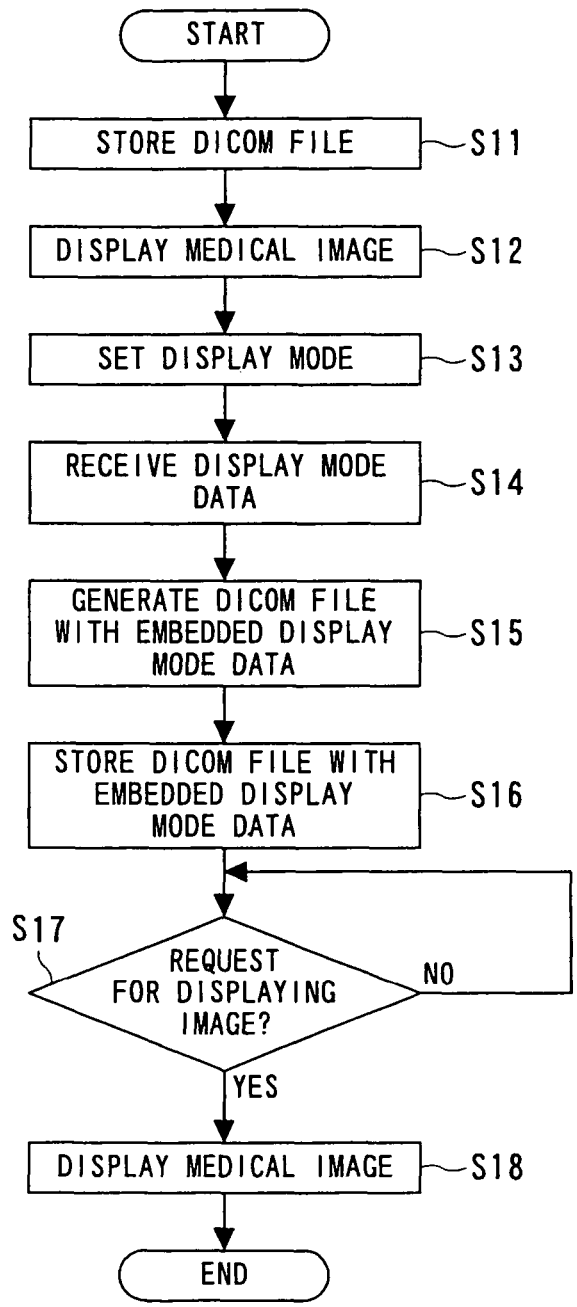
FIG. 8 illustrates a display mode of medical images that has been changed on a client viewer screen.

FIG. 8 illustrates a flow chart of a method for managing and displaying medical images according to another embodiment of the present invention using the system 10 for managing and displaying medical images. Since the system structure of this embodiment is the same as the system structures illustrated in FIGS. 1 and 3, descriptions on the system structure are omitted. In the following, the arrangement of images captured by multiple modalities is described. In the method for managing and displaying medical images described below, the combination of more than one modality can be realized, i.e., the combination of CT device 9a, the MR device 9b, and the CR device 9c. However, the combination of modalities is not limited to these devices.

First, when imaging for each patient is carried out by the CT device 9a, the MR device 9b, and the CR device 9c, a DICOM file is generated for CT image data, MR image data, and CR image data, illustrated in FIG. 1.

The controlling unit (not shown in the drawing) controls the system to send the DICOM files to the image file receiving unit 21 of the image storage server 12, illustrated in FIG. 3, via the LAN 15 and to store the DICOM files in the image file storage unit 22 (Step S11).

A user, such as a doctor or a nurse, turns on the power to start up the client viewer 13. The user operates a pointing device (not shown in the drawing), such as a mouse, to request for displaying the medical images about the patient M that is a certain patient.

DICOM files, including the medical image data, about the patient M is retrieved from the image file storage unit 22, stored in Step S11. These DICOM files are sent from the Web service unit 23 to the Web browser of the client viewer 13 via the LAN 15. If DICOM files, including the CT image data, MR image data and CR image data, about the patient M are stored at the image file storage unit 22, these DICOM files are sent to the Web browser of the client viewer 13. Using the DICOM files sent from the image storage server 12, the CT images, the MR images, and the CR image of the patient M are displayed on the client viewer 13 screen (Step S12).

The user operates the pointing device, i.e., mouse, to organize the CT images, the MR images, and the CR image through the GUI in an easily viewable arrangement. By dragging and dropping the CT images, the MR images, and the CR image, the user changes at least one of the image modes, i.e., the screen division, the image segment including the image, whether or not the image is included in a stack, or the order of the image in the stack, or the magnification of the image.

Figure 9:
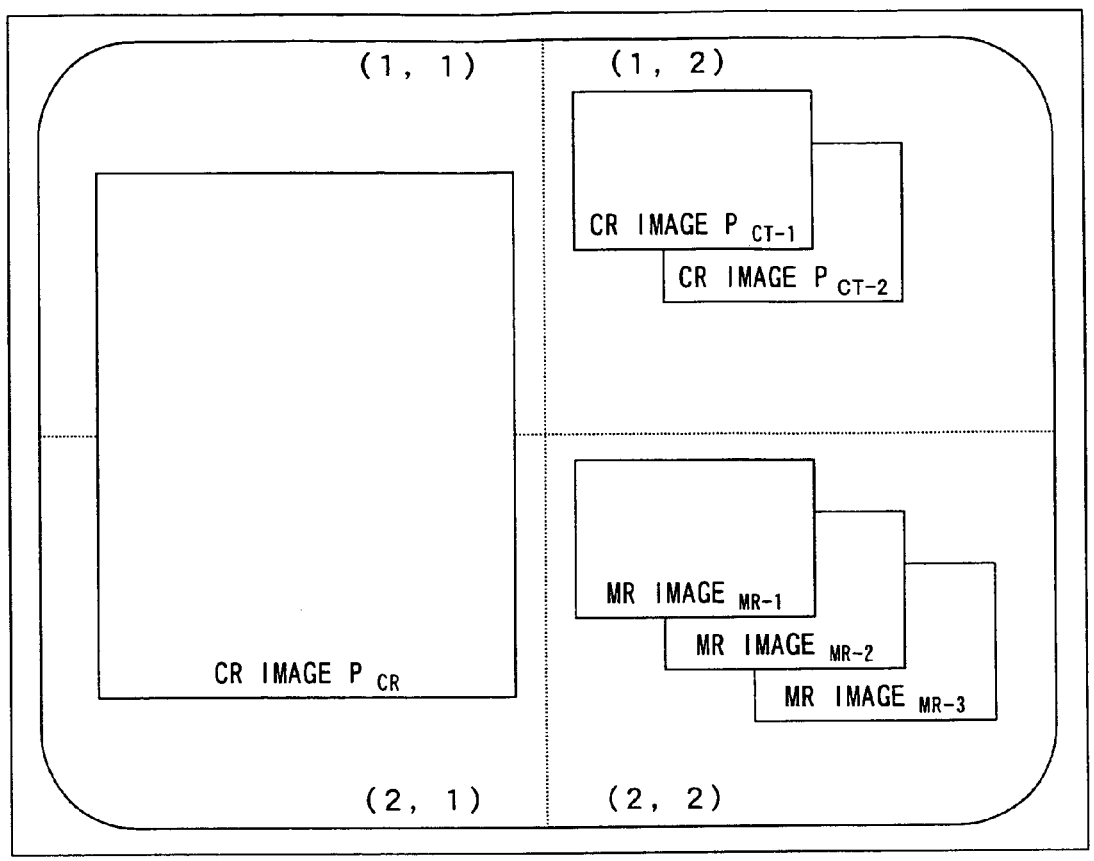
FIG. 9 illustrates a sample of a display mode of CT images, MR images and CR image after the display mode has been changed on the client viewer screen.

FIG. 9 illustrates a sample of a display mode of the CT images, MR images and CR image after the display mode has been changed on the client viewer 13 screen.

FIG. 9 illustrates the client viewer 13 screen after the display mode of CT images $P_{CT}$, MR images $P_{MR}$, and CR image $P_{CR}$ of the patient M has been changed in Step S12 such that the user can easily view the CT images, MR images, and CR image. For example, there are two CT images $P_{CT\text{-}1}$ and $P_{CT\text{-}2}$, three MR images $P_{MR\text{-}1}$, $P_{MR\text{-}2}$, and $P_{MR\text{-}3}$, and a CR image $P_{CR}$.

The display screen, as illustrated in FIG. 9, is divided into "2×2" segments. The "(1,2)" segment displays the CT images $P_{CT}$ in a stack at a magnification of "0.5."

The "(2,2)" segment of the display screen divided into "2×2" segments displays the MR images $P_{MR}$ in a stack at a magnification of "1."

The "(1,1)" and "(2,1)" segments ("(1,1)-(2,1)") of the display screen divided into "2×2" segments displays the CR image $P_{CR}$ without using stacking at a magnification of "1."

Next, the user carries out an operation to output the display mode data, such as clicking an output button on the client viewer 13 screen. Outputting the display mode data sets the display mode on the client viewer 13 screen (Step S13).

Once the display mode for the screen is set, the display mode data on every image is sent from the client viewer 13 to the display mode data receiving unit 25 of the image storage server 12 via the LAN 15. For example there are the display mode data $I_{CT\text{-}1}$, $I_{CT\text{-}2}$, $I_{MR\text{-}1}$, $I_{MR\text{-}2}$, $I_{MR\text{-}3}$, and $I_{CR}$ as the display mode data I.

FIG. 10A and FIG. 10B illustrate a sample of the display mode data I as a table.

FIG. 10A illustrates after the display mode data $I_{CT\text{-}1}$, $I_{CT\text{-}2}$, $I_{MR\text{-}1}$, $I_{MR\text{-}2}$, $I_{MR\text{-}3}$, and $I_{CR}$ are set as illustrated in FIG. 9. The display mode data $I_{CT\text{-}1}$, $I_{CT\text{-}2}$, $I_{MR\text{-}1}$, $I_{MR\text{-}2}$, $I_{MR\text{-}3}$, and $I_{CR}$ include the screen division, the image segment including the image, whether or not the image is included in a stack, and the magnification of the image.

For example, the display mode data $I_{CT\text{-}1}$ and $I_{CT\text{-}2}$ to conform to CT image $P_{CT\text{-}1}$ and $P_{CT\text{-}2}$ is "2×2, (1,2),S,0.5". That display mode data $I_{CT\text{-}1}$ and $I_{CT\text{-}2}$ represent that the screen division is "2×2", the image segment including the CT images is "(1,1)", the CT images are included a stack, and the magnification is "0.5", respectively. The display mode data $I_{MR\text{-}1}$, $I_{MR\text{-}2}$, and $I_{MR\text{-}3}$ to conform to MR image $P_{MR\text{-}1}$, $P_{MR\text{-}2}$, and $P_{MR\text{-}3}$ is "2×2, (2,2),S,1". That display mode data $I_{MR\text{-}1}$, $I_{MR\text{-}2}$, and $I_{MR\text{-}3}$ represent that the screen division is "2×2", the image segment including the MR images is "(2,2)", the MR images are included a stack, and the magnification is "1", respectively. The display mode data $I_{CR}$ to conform to CR image $P_{CR}$ is "2×2, (1,1)-(2,1),0,1". That display mode data $I_{CR}$ represents that the screen division is "2×2", the image segment including the CR image is "(1,1)-(2,1)", the CR image is not included a stack, and the magnification is "1", respectively.

As illustrated in FIG. 9, when medical images, made at some kinds of modalities, are lined up and displayed on the screen, the display mode data may be expressed in the unified form. For example, when two CT images, three MR images, and a CR image are lined up and displayed on the screen, the display mode data $I_{CT\text{-}1}$, $I_{CT\text{-}2}$, $I_{MR\text{-}1}$, $I_{MR\text{-}2}$, $I_{MR\text{-}3}$, and $I_{CR}$ to conform to CT image $P_{CT\text{-}1}$, $P_{CT\text{-}2}$, $P_{MR\text{-}1}$, $P_{MR\text{-}2}$, $P_{MR\text{-}3}$, and $P_{CR}$ is "2×2,CT-(1,2),CT-S,CT-0.5,MR-(2,2),MR-S,MR-1, CR-(1,1)-(2,1),CR-0,CR-1", As illustrated in FIG. 10B. That display mode data I represents that the screen division is "2×2", the image segment including the CT images is "(1,2)", the CT images are included a stack, and the magnification is "0.5", the image segment including the MR images is "(2,2)", the MR images are included a stack, and the magnification is "1", the image segment including the CR image is "(1,1)-(2, 1)", the CR image is not included a stack, and the magnification is "1", respectively.

Next, display mode data I sent from the client viewer 13, illustrated in FIG. 3, is received by the display mode data receiving unit 25 of the image storage server 12 (Step S14). Then this data is sent to the display mode data embedding unit 26. At the display mode data embedding unit 26, the display mode data I, received in Step S14, is embedded into each DICOM file to generate DICOM files F with embedded display mode data (Step S15). In the data element included in each DICOM file, tag and data length are embedded as binary data and tag data is embedded as text data (character string) or binary data.

The DICOM files F with embedded display mode data generated at the display mode data embedding unit 26, are stored in the image file storage unit 22 of the image storage server 12, illustrated in FIG. 3 (Step S16). The image storage server 12 enters a stand-by mode and waits for a request for displaying the medical images. At the same time, the image storage server 12 determines whether or not a request for displaying the medical images is made from the client viewer 13 (Step S17).

If an answer in Step S17 is determined to be "YES," i.e., a request is made from the client viewer 13 to display the medical images about the patient M, the DICOM files F for the patient M with embedded display mode about the patient M is retrieved from the image file storage unit 22, stored in Step S16. These DICOM files are sent from the Web service unit 23 to the Web browser of the client viewer 13 via the LAN 15. For example, if the DICOM files $F_{CT\text{-}1}$, $F_{CT\text{-}2}$, $F_{MR\text{-}1}$, $F_{MR\text{-}2}$, $F_{MR\text{-}3}$, and $F_{CR}$ with embedded display mode data $I_{CT\text{-}1}$, $I_{CT\text{-}2}$, $I_{MR\text{-}1}$, $I_{MR\text{-}2}$, $I_{MR\text{-}3}$, and $I_{CR}$ stored in the image file storage unit 22 respectively, the DICOM files $F_{CT\text{-}1}$, $F_{CT\text{-}2}$, $F_{MR\text{-}1}$, $F_{MR\text{-}2}$, $F_{MR\text{-}3}$, and $F_{CR}$ are sent from the Web service unit 23 to the Web browser of the client viewer 13 via the LAN 15.

On the client viewer 13 screen, the CT images $P_{CT\text{-}1}$, $P_{CT\text{-}2}$, the MR images $P_{MR\text{-}1}$, $P_{MR\text{-}2}$, $P_{MR\text{-}3}$, and the CR image $P_{CR}$ of the patient M are displayed in accordance with the display mode data $I_{CT\text{-}1}$, $I_{CT\text{-}2}$, $I_{MR\text{-}1}$, $I_{MR\text{-}2}$, $I_{MR\text{-}3}$, and $I_{CR}$, respectively. In other words, the CT images $P_{CT\text{-}1}$, $P_{CT\text{-}2}$, $P_{MR\text{-}1}$, $P_{MR\text{-}2}$, $P_{MR\text{-}3}$, and $P_{CR}$ of the patient M are initially displayed on the client viewer 13 screen in a display mode illustrated in FIG. 9 (Step S18). The CT images and the MR images, included in the stack, are sorted by an image number, an image UID (Unique IDentifier), or a preparation time.

The user may operate the medical images $P_{CT-1}$, $P_{CT-2}$, $P_{MR-1}$, $P_{MR-2}$, $P_{MR-3}$, and $P_{CR}$ of the patient M, displayed in Step S18, through the GUI by dragging and dropping the medical images using a pointing device, such as a mouse, to arrange the medical images in an arrangement that is easily viewable for the user. Subsequently, the new display mode is output, and the newly set display mode data is written over the tag data of the DICOM files F for the patient M with embedded display mode data and the medical images. Then, the process is returned to Step S16.

If an answer in Step S17 is determined to be "NO," i.e., a request is not made from the client viewer 13 to display the medical images about the patient M, the display mode data is updated, and the process is returned to Step S17. Then, the image storage server 12 enters a stand-by mode and waits for a request for displaying the medical images.

Medical images captured by multiple modalities other than the CT device 9a, the MR device 9b, and the CR device 9c are also displayed in accordance with the tag information in the same manner as the image captured by the multiple modalities of the CT device 9a, the MR device 9b, and the CR device 9c as described above.

Furthermore, the multiple modality viewer may be required to use image data such as computer aided diagnosis or detection (CAD) data to display similar images on the screen of the client viewer 13 or to box off a predetermined image and line up similar images next to the boxed off image. In such a case, a dot representing the starting point at the edge of an image (for example, the top left corner), and the dot representing the ending point at the edge of the image, (for example, the bottom right corner), may be embedded into each DICOM files.

For example, the top left corner and the bottom right corner of the image "(50,50)-(600,600)" are embedded into each DICOM files. The medical image including the top left corner and the bottom right corner of the image "(50,50)-(600,600)" will be displayed such that the top left corner of the image matches the dot coordinate (50,50) on the client viewer 13 screen and the bottom right corner of the image matches the dot coordinate (600,600) on the client viewer 13 screen.

The tag data "(50,50)-(600,600), S1" may be embedded to indicate the top left corner and the bottom right corner of the image and indicate that the image is included in a stack.

FIG. 11 illustrates a sample of the display mode data I as a table.

FIG. 11 illustrates the display mode data $I_{CT-1}$, $I_{CT-2}$, $I_{MR-1}$, $I_{MR-2}$, $I_{MR-3}$, and $I_{CR}$, after the display mode for the screen of CT images $P_{CT-1}$, $P_{CT-2}$, MR images $P_{MR-1}$, $P_{MR-2}$, $P_{MR-3}$, and CR image $P_{CR}$ are set as illustrated in FIG. 9. The display mode data $I_{CT-1}$, $I_{CT-2}$, $I_{MR-1}$, $I_{MR-2}$, $I_{MR-3}$, and $I_{CR}$ include the user who logged in to the network N (user ID), the screen division, the image segment including the image, whether or not the image is included in a stack, and the order of the image in the stack.

For example, the display mode data $I_{CT-1}$ and $I_{CT-2}$ to conform to CT image $P_{CT-1}$ and $P_{CT-2}$ is "A12345, 2×2, (1,2),S, 0.5". That display mode data $I_{CT-1}$ and $I_{CT-2}$ represent that the user ID is "A12345", the screen division is "2×2", the image segment including the CT images is "(1,1)", the CT images are included a stack, and the magnification is "0.5", respectively. The display mode data $I_{MR-1}$, $I_{MR-2}$, and $I_{MR-3}$ to conform to CT image $P_{MR-1}$, $P_{MR-2}$, and $P_{MR-3}$ is "A12345, 2×2, (2,2),S,1". That display mode data $I_{MR-1}$, $I_{MR-2}$, and $I_{MR-3}$ represent that the user ID is "A12345", the screen division is "2×2", the image segment including the MR images is "(2,2)", the MR images are included a stack, and the magnification is "1", respectively. The display mode data ICR to conform to CT image $P_{CR}$ is "A12345, 2×2,(1,1)-(2,1),0,1". That display mode data $I_{CR}$ represents that the user ID is "A12345", the screen division is "2×2", the image segment including the CR image is "(1,1)-(2,1)", the CR image is not included a stack, and the magnification is "1", respectively.

The method for managing and displaying medical images using the system 10 for managing and displaying medical images displays the medical images in an appropriate display mode at the initial settings and thus is capable of improving the working efficiency for the user.

According to the method for managing and displaying medical images using the system 10 for managing and displaying medical images, image identification numbers according to the categorization of the examination do not have to be managed and the load on the network is reduced.

According to the method for managing and displaying medical images using the system 10 for managing and displaying medical images, the display mode of the initial display of the medical images can be controlled by the image storage server 12.

According to the method for managing and displaying medical images using the system 10 for managing and displaying medical images, the display positions of the medical images can be set for each medical image and various display modes of the medical images may be employed. Since various settings are possible for a medical image, the method may be applied as a display layout preset function.

Figure 12:
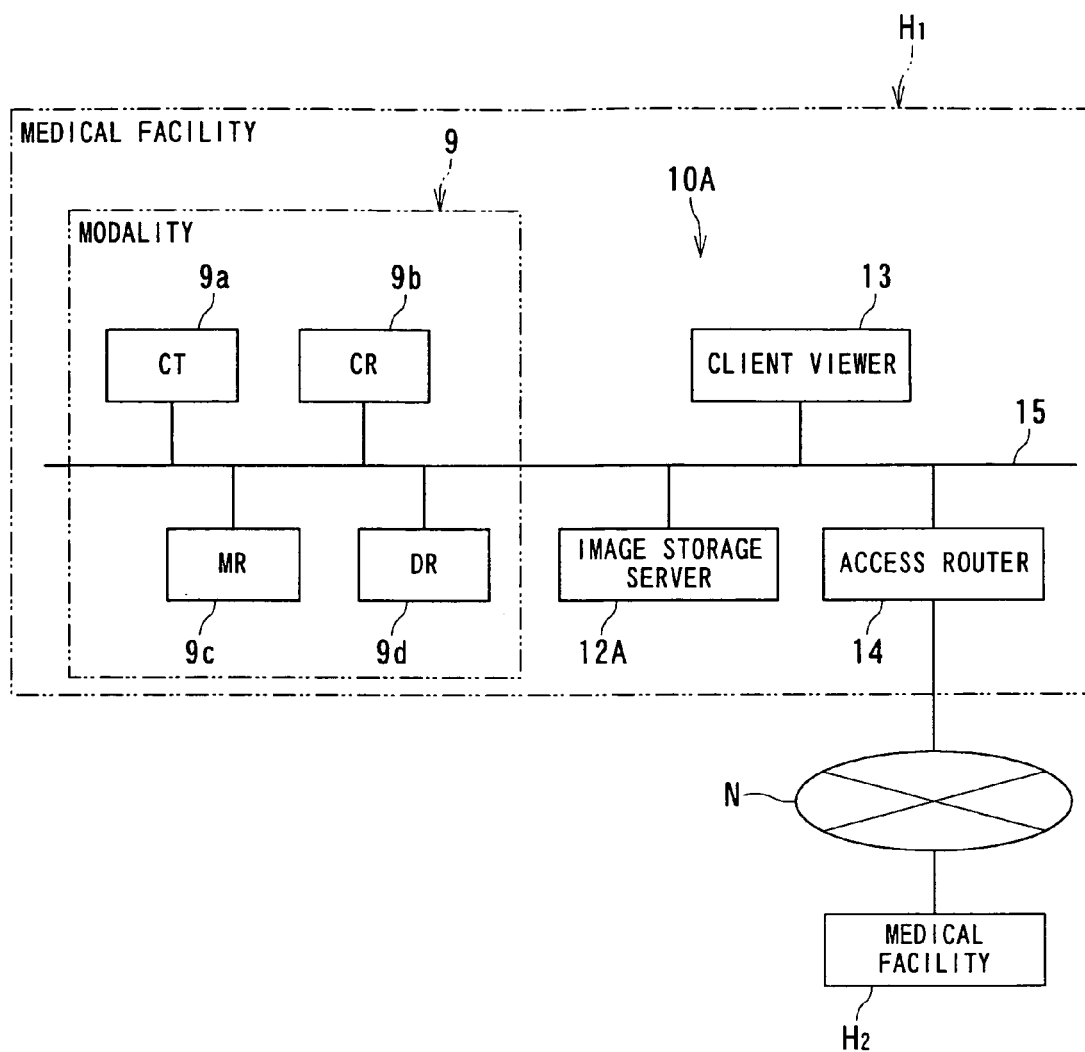
FIG. 12 is a schematic view of the entire system for managing and displaying medical images.
Figure 13:
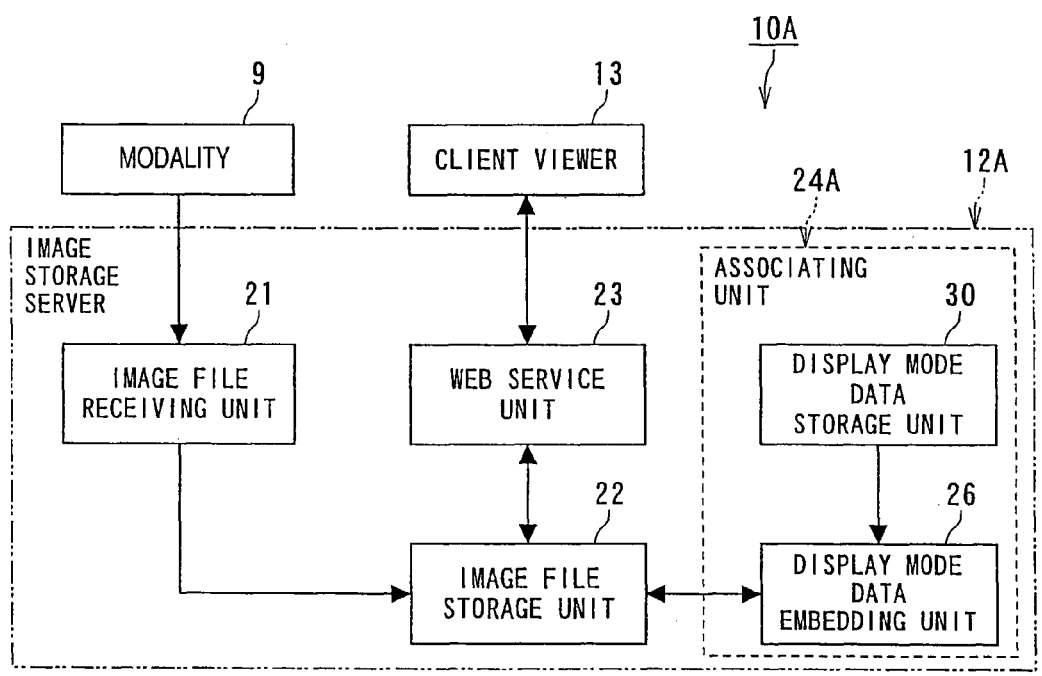
FIG. 13 is a block diagram illustrating the image storage server according to a second embodiment of the present invention.

FIGS. 12 and 13 illustrate a system for managing and displaying medical images according to a second embodiment of the present invention. FIG. 12 illustrates the entire system for managing and displaying medical images. Furthermore, the same sign is put to the same composition member as the FIG. 1, and an explanation is omitted about the composition member of the FIG. 12.

FIGS. 13 is a block diagram illustrating the image storage server 12A.

The image storage server 12A, illustrated in FIG. 13, includes an associating unit 24A for associating the image files, including the medical image data, with the display mode data held at least a screen division and an image segment including the medical images. The associating unit 24A includes, for example, a display mode data storage unit 30 for storing the display mode data. The display mode data storage unit 30 stores in advance the display mode data to display medical images on the screen of the client viewer 13. The DICOM files F with embedded display mode data is generated by embedding the display mode data into the DICOM files. Furthermore, the same sign is put to the same composition member as the FIG. 3, and an explanation is omitted about the composition member of the FIG. 13. In this case, at the associating unit 24A, the display mode data is embedded into the DICOM files. However, associating is not limited to embed the display mode data into the DICOM files.

FIG. 14 illustrates a sample of the display mode data I as a table.

The display mode data storage unit 30 stores a comparison table a display mode data I with a classification of the medical image data. For example, the medical image data is classified by a modality kind, a station's name kind, an AE (Application Entity) title kind, an image matrix kind, or a fusion kind.

If the medical image data, classified by the modality kind, includes only CT image data, the display mode data I includes "2×2,CT-(1,1)-(2,2),CT-S,CT-0.5". That display mode data I represents that the screen division is "2×2", the CT image segment including the CT images is "(1,1)-(2,2)", the CT images are included in a stack, and the magnification is "0.5". If the medical image data, classified by the modality kind, includes, the CT image data, the MR image data, and the CR image data, the display mode data I includes "2×2, CT-(1,2), CT-S,CT-0.5,MR-(2,2),MR-S,MR-1,CR-(1,1)-(2,1),CR-0, CR-1". That display mode data I represents that the screen division is "2×2", the CT image segment including the CT images is "(1,2)", the CT images are included in a stack, the magnification is "0.5", the MR image segment including the MR images is "(2,2)", the MR images are included in a stack, the magnification is "1", the CR image segment including the CR image is "(1,1)-(2,1)", the CR image is not included in a stack, and the magnification is "1".

When the images, acquired at one modality 9, are displayed on the client viewer 13 screen, the display mode data of these images may be embedded into the DICOM files at the modality 9.

The image storage server 12A of the system 10A includes the associating unit 24A. Then, at the image storage server 12A, the display mode data is embedded into the each DICOM file in accordance with a comparison table, stored at the display mode data storage unit 30. Because the image storage server 12A stores image data, including various kinds of modalities, the display mode can set the arrangement of images captured by multiple modalities.

However, the modality 9 or client viewer 13, illustrated in FIG. 1 and FIG. 3, may include the associating unit 24A.

Figure 15:
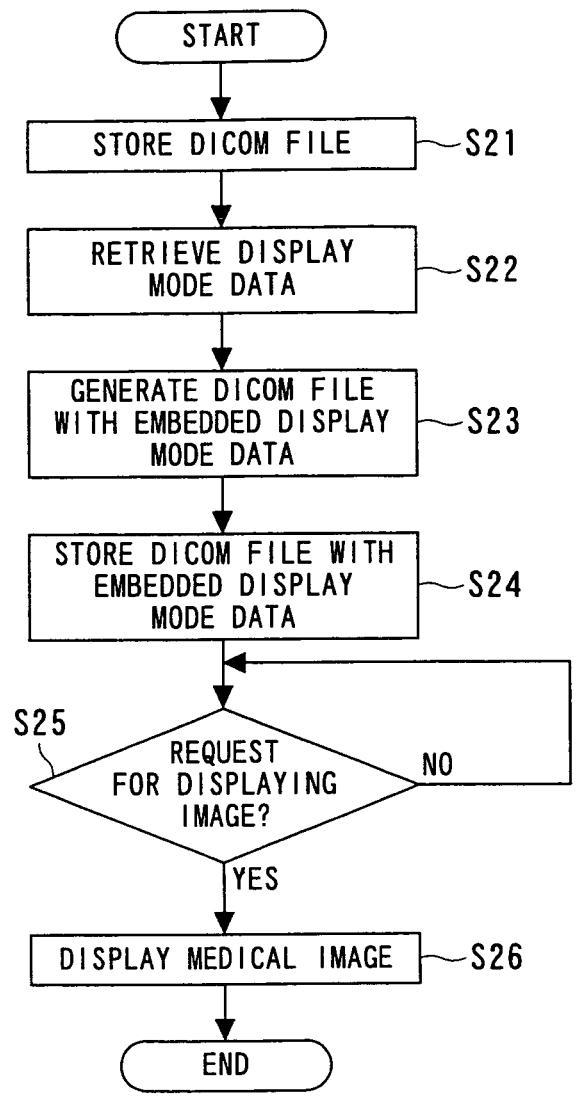
FIG. 15 is a flow chart illustrating a method for managing and displaying medical images according to an embodiment of the present invention.

Next, the method for managing and displaying medical images using the system 10A for managing and displaying medical images will be described with reference to the flow chart in FIG. 15. In this case, the arrangement of images captured by multiple modalities is described. In the method for managing and displaying medical images described below, the modalities 9 include the CT device 9a, the MR device 9b and the CR device 9c. However, the modalities 9 are not limited to these devices.

First, when imaging for each patient is carried out by the CT device 9a, the MR device 9b, and the CR device 9c, a DICOM file is generated for each medical image data, illustrated in FIG. 12.

The controlling unit (not shown in the drawing) controls the system to send the DICOM files to the image file receiving unit 21 of the image storage server 12A, illustrated in FIG. 13, via the LAN 15 and to store the DICOM files in the image file storage unit 22 (Step S21).

The display mode data I, compared with the classification of the medical image data, is read from the display mode data storage unit 30 (Step S22). For example, when CT image data, MR image data, and CR image data are stored in the image storage server 12, "2×2,CT-(1,2),CT-S,CT-0.5,MR-(2,2), MR-S,MR-1,CR-(1,1)-(2,1),CR-0,CR-1", illustrated in FIG. 14, is read from the display mode data 30.

The display mode data I, read in Step S22, is embedded into the DICOM files to generate DICOM files F with embedded display mode data (Step S23). These DICOM files F are stored in the image file storage unit 22 of the image storage server 12A (Step S24). For example, the DICOM files including two CT image data generate the DICOM files $F_{CT-1}$ and $F_{CT-2}$. The DICOM files including three MR image data generate the DICOM files $F_{MR-1}$, $F_{MR-2}$, and $F_{MR-3}$. The DICOM file including a CR image data generates the DICOM file $F_{CR}$.

The image storage server 12A enters a stand-by mode and waits for a request for displaying the medical images. At the same time, the image storage server 12A determines whether or not a request for displaying the medical images is made from the client viewer 13 (Step S25).

If an answer in Step S25 is determined to be "Yes," i.e., a request is made from the client viewer 13 to display the medical images about the patient M, DICOM files F for the patient M with embedded display mode data about the patient M are retrieved from the image file storage unit 22, stored in Step S24. These DICOM files F are sent from the Web service unit 23 to the Web browser of the client viewer 13 via the LAN 15. For example, if the DICOM files $F_{CT-1}$, $F_{CT-2}$, $F_{MR-1}$, $F_{MR-2}$, $F_{MR-3}$, and $F_{CR}$ with embedded display mode data $I_{CT-1}$, $I_{CT-2}$, $I_{MR-1}$, $I_{MR-2}$, $I_{MR-3}$, and $I_{CR}$ stored in the image file storage unit 22 respectively, the DICOM files $F_{CT-1}$, $F_{CT-2}$, $F_{MR-1}$, $F_{MR-2}$, $F_{MR-3}$, and $F_{CR}$ are sent from the Web service unit 23 to the Web browser of the client viewer 13 via the LAN 15.

On the client viewer 13 screen, the CT images $P_{CT-1}$ and $P_{CT-2}$, the MR images $P_{MR-1}$, $P_{MR-2}$, and $P_{MR-3}$, and the CR image $P_{CR}$ of patient M are initially displayed in accordance with the display mode data $I_{CT-1}$, $I_{CT-2}$, $I_{MR-1}$, $I_{MR-2}$, $I_{MR-3}$, and $I_{CR}$, respectively (Step S26).

If an answer in the Step S25 is determined to be "NO," i.e., a request is not made from the client viewer 13 to display the medical images about the patient M, the process is returned to Step S25. Then, the image storage server 12A enters a stand-by mode and waits for a request for displaying the medical image.

Figure 16:
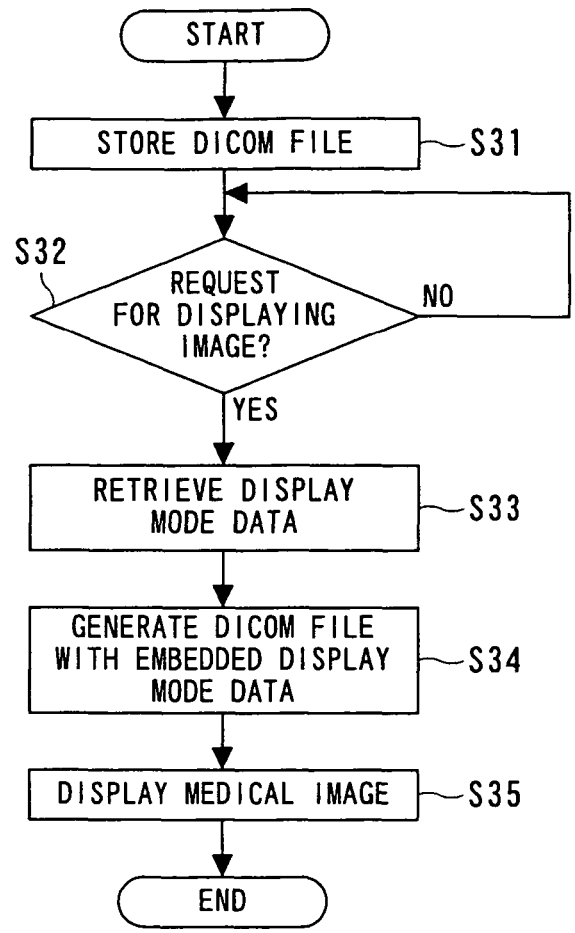
FIG. 16 illustrates a flow chart of a method for managing and displaying medical images according to another embodiment of the present invention using the system 10A for managing and displaying medical images.

FIG. 16 illustrates a flow chart of a method for man aging and displaying medical images according to another embodiment of the present invention using the system 10A for managing and displaying medical images. Since the system structure of this embodiment is the same as the system structures illustrated in FIGS. 12 and 13, description on the system structure are omitted. In the following, the arrangement of images captured by multiple modalities is described. In the method for managing and displaying medical images described below, the modalities 9 include the CT device 9a, the MR device 9b, and the CR device 9c. However, the modalities 9 are not limited to these devices.

First, when imaging for each patient is carried out by the CT device 9a, the MR device 9b, and the CR device 9c, a DICOM file is generated for each medical image data, illustrated in FIG. 12.

The controlling unit (not shown in the drawing) controls the system to send the DICOM files to the image file receiving unit 21 of the image storage server 12A, illustrated in FIG. 13, via the LAN 15 and to store the DICOM files in the image file storage unit 22 (Step S31).

The image storage server 12A enters a stand-by mode and waits for a request for displaying the medical images. At the same time, the image storage server 12A determines whether or not a request for displaying the medical images is made from the client viewer 13 (Step S32).

If an answer in Step S32 is determined to be "Yes," i.e., a request is made from the client viewer 13 to display the medical images about the patient M, the display mode data I, compared with the classification of the medical image data, is read from the display mode data 30 (Step S33). These display mode data I, read in Step S33, is embedded into the DICOM files to generate DICOM files F with embedded display mode data. (Step S34). For example, the DICOM files including two CT image data generate the DICOM files $F_{CT-1}$ and $F_{CT-2}$. The DICOM files including three MR image data generate the DICOM files $F_{MR-1}$, $F_{MR-2}$, and $F_{MR-3}$. The DICOM file including a CR image data generates the DICOM file $F_{CR}$.

The DICOM files F with embedded display mode data I, respectively are sent from the Web service unit 23 to the Web browser of the client viewer 13 via the LAN 15.

On the client viewer 13 screen, the CT images $P_{CT-1}$ and $P_{CT-2}$, the MR images $P_{MR-1}$, $P_{MR-2}$, and $P_{MR-3}$, and the CR image $P_{CR}$ of patient M are initially displayed in accordance with the display mode data $I_{CT-1}$, $I_{CT-2}$, $I_{MR-1}$, $I_{MR-2}$, $I_{MR-3}$, and $I_{CR}$, respectively (Step S35).

If an answer in the Step S32 is determined to be "NO," i.e., a request is not made from the client viewer 13 to display the medical images about the patient M, the process is returned to Step S32. Then, the image storage server 12 enters a stand-by mode and waits for a request for displaying the medical image.

Furthermore, the multiple modality viewer may be required to use image data such as CAD data to display similar images on the screen of the client viewer 13 or to box off a predetermined image and line up similar images next to the boxed off image. In such a case, the dot representing the starting point at the edge of an image (for example, the top left corner), and the dot representing the ending point at the edge of the image, (for example, the bottom right corner), may be embedded into each DICOM file.

The method for managing and displaying medical images using the system 10A for managing and displaying medical images displays the medical images in an appropriate display mode at the initial settings and thus is capable of improving the working efficiency for the user.

According to the method for managing and displaying medical images using the system 10A for managing and displaying medical images, image identification numbers according to the categorization of the examination do not have to be managed and the load on the network is reduced.

According to the method for managing and displaying medical images using the system 10A for managing and displaying medical images, the display mode of the initial display of the medical images can be controlled by the image storage server 12A.

According to the method for managing and displaying medical images using the system 10A for managing and displaying medical images, the display positions of the medical images can be set for each medical image and various display modes of the medical images may be employed. Since various settings are possible for a medical image, the method may be applied as a display layout preset function.

What is claimed is:

1. A system for managing and displaying medical images, comprising:
    an image display unit configured to display data of medical images;
    a user operated input unit configured to position the medical images on the image display unit and to set a display mode to set the positioned medical images in the display mode;
    an image file generating unit configured to generate an image file including data of the medical images and incidental data that includes display mode data and a classified kind of the medical images, which classified kind of the medical image is a modality kind, an image matrix kind, or a fusion kind;
    an adding unit configured to add the display mode data for each classified kind of the medical image into the image file, the display mode data for each classified kind of the medical image indicating, based on the positions of the medical images set in the display mode by the user, at least a number of screen divisions, display positions formed by the screen divisions, and an indication of the classified kind of each of plural of medical images formed within the screen divisions, in which each display position corresponds to a single classified kind of medical image when medical images corresponding to different classified kinds are concurrently displayed on a screen;
    an obtaining unit configured to obtain an image file including the display mode data in the incidental data among the added image files; and
    an image display unit configured to display the respective medical images included in the obtained image files on the screen in accordance with the display mode data added in the obtained image files.

2. The system for managing and displaying medical images, according to claim 1, wherein
    the adding unit adds post-operational display mode data, decided by operating the respective medical images, included in the obtained image files and displayed on the screen, into the obtained image files.

3. The system for managing and displaying medical images, according to claim 1, further comprising:
    an association table storage unit configured to store an association table in which the display mode data is associated with the respective classified kinds of medical images; wherein
    the adding unit adds the display mode data into the generated image file corresponding to the classified kind included in the image file by referring to the association table.

4. The system for managing and displaying medical images, according to claim 1, wherein
    the adding unit adds the display mode data into the image file in every user or every display unit including the screen.

5. The system for managing and displaying medical images, according to claim 1, wherein
    the adding unit embeds the display mode data into the image file.

6. The system for managing and displaying medical images, according to claim 1, wherein
    the adding unit adds a secondary display mode data into the image file, indicating the display position of one medical image if the one medical image is displayed on the screen.

7. A method for managing and displaying medical images, comprising:
    (A) displaying data of medical images;
    (B) positioning, through a user operated input unit, the medical images on the image display unit and to set a display mode to set the positioned medical images in the display mode:
    (C) generating an image file including data of the medical images and incidental data that includes display mode data and a classified kind of the medical images, which classified kind of the medical images is a modality kind, an image matrix kind, or a fusion kind;
    (D) adding the display mode data for each classified kind of the medical image into the image file, the display mode data for each classified kind of the medical image indicating, based on the positions of the medical images set in the display mode by the user, at least a number of display positions formed by the screen divisions, and an indication of the classified kind of each of plural of medical images formed within the screen divisions, in which each display position corresponds to a single classified kind of medical image when medical images corresponding to different classified kinds are concurrently displayed on a screen;
    (E) obtaining an image file including the display mode data in the incidental data among the added image files; and (F) displaying the respective medical images included in the obtained image files on the screen in accordance with the display mode data added in the obtained image files.

8. The method for managing and displaying medical images, according to claim 7, further comprising:
temporarily displaying the respective medical images included in the obtained image files on the screen;
wherein
the adding (D) adds post-operational display mode data into the obtained image files if the post-operational display mode data is decided by operating the respective medical images included in the obtained image files and displayed on the screen.

9. The method for managing and displaying medical images, according to claim 7, wherein
the adding (D) embeds the display mode data into the image file.

10. The method for managing and displaying medical images, according to claim 7, wherein
the adding (D) adds the display mode data into the image file in every user or every display unit including the screen.

11. The method for managing and displaying medical images, according to claim 7, further comprising:
storing an association table which the display mode data associates the respective classified kinds,
wherein
the adding (D) adds the display mode data into the generated image file corresponding to the classified kind included in the image file by referring to the association table.

12. The method for managing and displaying medical images, according to claim 7, wherein the display mode data further includes data on at least one of a usage of a display by a stack, the number of medical images in the stack, and a magnification of the medical images.

13. The method for managing and displaying medical images, according to claim 7, wherein the respective display positions are represented by a dot corresponding to a starting point at an edge of the medical image, and a dot corresponding to an ending point at the edge of the medical image.

14. The method for managing and displaying medical images, according to claim 7, wherein the display mode data is embedded into a blank area, a standard tag data of a patient demographic data area, or a private tag data of the patient demographic data area included in a DICOM file as the image file.

15. The method for managing and displaying medical images, according to claim 7, wherein the display mode data, added in the image file, is updated after the display mode data is changed.

16. The method for managing and displaying medical images, according to claim 7, wherein
the display mode data added by the adding (D) is different according to the classified kind and the number of the classified kinds.

17. A system for managing and displaying medical images, comprising:
an image display unit configured to display data of medical images;
a user operated input unit configured to position the medical images on the image display unit and to set a display mode to set the positioned medical images in the display mode;
an image file generating unit configured to generate an image file including data of the medical images and incidental data that includes display mode data and a classified kind of the medical images, which classified kind of the medical image is a modality kind, an image matrix kind, or a fusion kind;
an adding unit configured to add the display mode data for each classified kind of the medical image into the image file, the display mode data for each classified kind of the medical image indicating, based on the positions of the medical images set in the display mode by the user, at least a number of screen divisions, display positions formed by the screen divisions, and an indication of the classified kind of each of plural of medical images formed within the screen divisions, in which each display position corresponds to a single classified kind of medical image when medical images corresponding to the classified kinds are concurrently displayed on a screen; and
the image display unit configured to display the respective medical images, included in image files among the added image files, on the screen in accordance with the display mode data added in the image files.

18. A method for managing and displaying medical images, comprising:
(A) displaying data of medical images;
(B) positioning, through a user operated input unit, the medical images on the image display unit and to set a display mode to set the positioned medical images in the display mode;
(C) generating an image file including data of the medical images and incidental data that includes display mode data and a classified kind of the medical images, which classified kind of the medical images is a modality kind, an image matrix kind, or a fusion kind;
(D) adding the display mode data for each classified kind of the medical image into the image file, the display mode data for each classified kind of the medical image indicating, based on the positions of the medical images set in the display mode by the user, at least a number of screen divisions and display positions formed by the screen divisions, and an indication of the classified kind of each of plural of medical images formed within the screen divisions, in which each display position corresponds to a single classified kind of medical image when medical images corresponding to the classified kinds are concurrently displayed on a screen; and
(E) displaying the respective medical images, included in image files among the added image files, on the screen in accordance with the display mode data added in the image files.

19. A system for managing and displaying medical images, comprising:
an image display unit configured to display data of medical images;
a user operated input unit configured to position the medical images on the image display unit and to set a display mode to set the positioned medical images in the display mode;
an associating unit configured to associate an image file including data of the medical images and a classified kind of the medical image, which classified kind of the medical image is a modality kind, an image matrix kind, or a fusion kind, with display mode data for each classified kind of the medical images indicating, based on the positions of the medical images set in the display mode by the user, at least a screen division and an image segment of the medical image; and an image display unit configured to display the medical image included in the image file on the screen in accordance with the display mode data associated with the image file.

* * * * *